(12) United States Patent
Ramos et al.

(10) Patent No.: US 12,224,069 B2
(45) Date of Patent: Feb. 11, 2025

(54) WORKSTATION ASSIGNMENT

(71) Applicant: International Business Machines Corporation, Armonk, NY (US)

(72) Inventors: Igor S. Ramos, Round Rock, TX (US); Kimberly J. Taft, Austin, TX (US); Angelo Danducci, II, Austin, TX (US); Devon E. Mensching, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 707 days.

(21) Appl. No.: 17/215,156

(22) Filed: Mar. 29, 2021

(65) Prior Publication Data

US 2022/0310262 A1  Sep. 29, 2022

(51) Int. Cl.
| | |
|---|---|
| *F24F 11/63* | (2018.01) |
| *G06N 5/04* | (2023.01) |
| *G06Q 10/02* | (2012.01) |
| *G06Q 10/0635* | (2023.01) |
| *G06Q 10/067* | (2023.01) |
| *G06Q 10/105* | (2023.01) |
| *G06Q 10/20* | (2023.01) |

(Continued)

(52) U.S. Cl.
CPC .............. *G16H 50/30* (2018.01); *F24F 11/63* (2018.01); *G06N 5/04* (2013.01); *G06Q 10/02* (2013.01); *G06Q 10/0635* (2013.01); *G06Q 10/067* (2013.01); *G06Q 10/105* (2013.01); *G06Q 10/20* (2013.01); *G16H 50/20* (2018.01); *G16H 50/80* (2018.01); *G16H 10/20* (2018.01)

(58) Field of Classification Search
CPC ........................... G16H 50/30; G06Q 10/0635
See application file for complete search history.

(56) References Cited

U.S. PATENT DOCUMENTS

| | | |
|---|---|---|
| 4,715,154 A | 12/1987 | Baloga |
| 6,318,113 B1 | 11/2001 | Levy |

(Continued)

FOREIGN PATENT DOCUMENTS

| | | |
|---|---|---|
| CN | 103796575 B | 3/2016 |
| CN | 107223195 B | 10/2019 |
| WO | 2018050198 A1 | 3/2018 |

OTHER PUBLICATIONS

Anonymous. "A safer and smarter return to the workplace." Printed Feb. 25, 2021. 9 pages. Published by IBM. https://www.ibm.com/watson/watson-works.

(Continued)

*Primary Examiner* — Reginald R Reyes
(74) *Attorney, Agent, or Firm* — Caleb D. Wilkes

(57) ABSTRACT

A processor may generate a workstation characteristics model of a workspace. A processor may generate respective user profiles for each of one or more users. Each of the respective user profiles may include user data associated with a respective user. A processor may assign, based on the respective user profiles, a respective risk level to each of the respective user profiles. A processor may compare each of the respective risk levels to a risk threshold level. A processor may apply a user characteristic model. A user characteristic model may be based on each of the respective risk levels and the workstation characteristics model. A processor may assign each of the one or more users to respective workstations based on the user characteristic model.

20 Claims, 5 Drawing Sheets

(51) Int. Cl.
*G16H 50/20* (2018.01)
*G16H 50/30* (2018.01)
*G16H 50/80* (2018.01)
*G16H 10/20* (2018.01)

(56) References Cited

U.S. PATENT DOCUMENTS

| | | |
|---|---|---|
| 9,844,344 B2 | 12/2017 | Horseman |
| 10,386,800 B2 | 8/2019 | Ahmed |
| 11,789,986 B1 * | 10/2023 | Bhimani ............... G06F 16/242 |
| | | 707/722 |
| 2006/0229896 A1 * | 10/2006 | Rosen ............... G06Q 10/1053 |
| | | 705/321 |
| 2017/0293866 A1 | 10/2017 | Bender |
| 2020/0134243 A1 * | 4/2020 | Vardi ............... G06F 30/27 |
| 2020/0163454 A1 | 5/2020 | Carson |

OTHER PUBLICATIONS

Anonymous. "COVID-19 Employer Information for Office Buildings." Published Jan. 4, 2021. Printed Feb. 25, 2021. 6 pages. Published by Centers for Disease Control and Prevention (CDC) https://www.cdc.gov/coronavirus/2019-ncov/community/office-buildings.html.

Anonymous. "Digital Twin Based HVAC Contamination Control." Published Aug. 7, 2020. 5 pages. Published by IP.com. https://ip.com/IPCOM/000263224.

Mell, et al., "The NIST Definition of Cloud Computing," Recommendations of the National Institute of Standards and Technology, U.S. Department of Commerce, Special Publication 800-145, Sep. 2011, 7 pgs.

Stewart, et al., "Ashrae Position Document on Infectious Aerosols." Published Apr. 14, 2020. 24 pages. Published by Ashrae. https://www.ashrae.org/file%20library/about/position%20documents/pd_infectiousaerosols_2020.pdf.

Zhuang, et al., "CFD study of the effects of furniture layout on indoor air quality under typical office ventilation schemes." Published in 2014. 13 pages. Build. Simul. 7, pp. 263-275. Published by Springer. https://doi.org/10.1007/s12273-013-0144-5.

\* cited by examiner

WORKSTATION ASSIGNMENT

BACKGROUND

The present disclosure relates generally to the field of epidemiology, and more particularly to techniques for reducing the spread of disease (e.g., COVID-19).

In the past, little concern was given regarding the layout of workstations in a workplace. The COVID-19 pandemic has altered how employers and employees view and interact in the workplace. As a result of COVID-19, many employers are making workstations and workplaces safer by mitigating an employee's risk of contracting communicable diseases in the workplace.

SUMMARY

Embodiments of the present disclosure include a method, computer program product, and system for workstation assignment. A processor may generate a workstation characteristics model of a workspace. A processor may generate respective user profiles for each of one or more users. Each of the respective user profiles may include user data associated with a respective user. A processor may assign, based on the respective user profiles, a respective risk level to each of the respective user profiles. A processor may compare each of the respective risk levels to a risk threshold level. A processor may apply a user characteristic model. A user characteristic model may be based on each of the respective risk levels and the workstation characteristics model. A processor may assign each of the one or more users to respective workstations based on the user characteristic model.

The above summary is not intended to describe each illustrated embodiment or every implementation of the present disclosure.

BRIEF DESCRIPTION OF THE DRAWINGS

The drawings included in the present disclosure are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
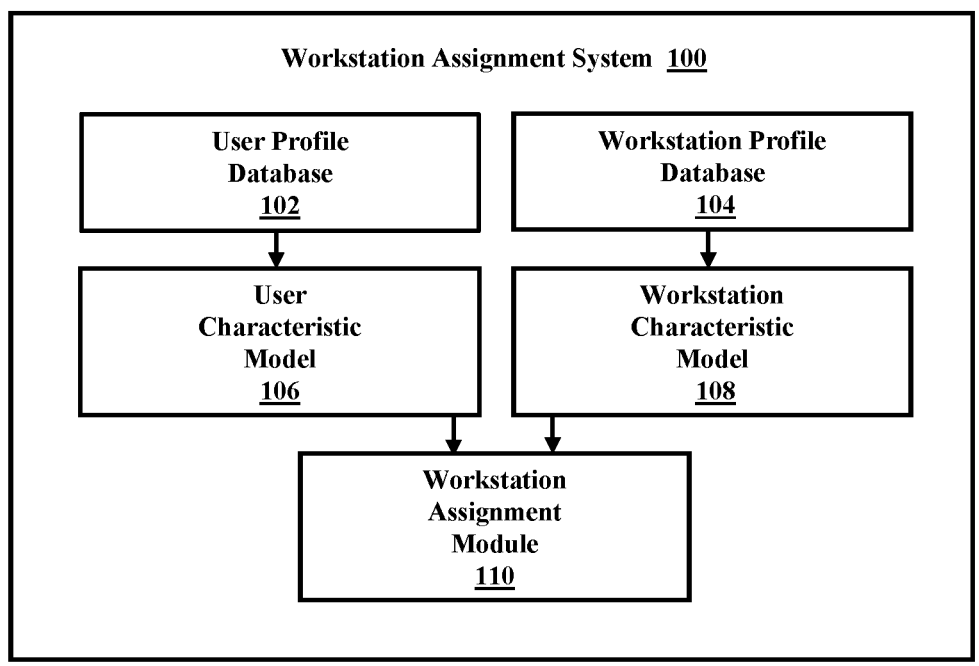
FIG. 1 illustrates a block diagram of a system for workstation assignment, in accordance with embodiments of the present disclosure.

While the embodiments described herein are amenable to various modifications and alternative forms, specifics thereof have been shown by way of example in the drawings and will be described in detail. It should be understood, however, that the particular embodiments described are not to be taken in a limiting sense. On the contrary, the intention is to cover all modifications, equivalents, and alternatives falling within the spirit and scope of the disclosure.

DETAILED DESCRIPTION

The present disclosure relates generally to the field of epidemiology, and more particularly to techniques for reducing the spread of disease, such as COVID-19. While the present disclosure is not necessarily limited to such applications, various aspects of the disclosure may be appreciated through a discussion of various examples using this context.

COVID-19 has resulted in employers having to change how employees operate in the workplace across different industries. While each workspace is unique, employers have often tried to mitigate the spread of COVID-19. Such methods have included, reducing the number of employees occupying a particular workspace, updating workspace cleaning schedules, requesting their employees answer COVID-19 health related questionnaires, and requiring COVID-19 testing when an employee meets specific criteria, such as an employee closely interacting with a person who has tested positive for COVID-19.

In embodiments discussed herein, are solutions provided in the form of a method, system, and computer program product for mitigating the risk of community spread of disease (e.g., COVID-19), and more particularly, for minimizing risk associated with daily exposure to disease in the workplace. While embodiments contemplated herein often refer to COVID-19, such embodiments may be applied to any airborne disease that may be spread in the workplace. Embodiments disclosed herein mitigate the risk of community spread by assigning workstations (e.g., desks, cubicles, offices, etc.) to employees who are working in the workplace/workspace.

In embodiments, a processor may be configured to receive or collect data from a check-in questionnaire. A check-in questionnaire may be filled out by users or employees who wish to work or occupy a workstation in the workspace. Often employers, when able, have offered their employees the opportunity to work remotely or work from home. The check-in questionnaire may ask the employee about their likelihood of coming into contact with a COVID-19 positive person and/or if they have any COVID-19 symptoms (e.g., cough or fever). Based on the answers to the check-in questionnaire, a processor may determine an employee has a low exposure risk of testing positive for COVID-19. In these embodiments, a processor may compare each of the exposure risk levels of the users/employees to a risk threshold level. While in some embodiments, a risk threshold level may be determined by an employer or owner of a workspace, in other embodiments, a risk threshold level may be determined by, or take into consideration, health and safety guidelines recommended by medical personnel.

In embodiments, where a processor determines an employee has an exposure risk level (e.g., of having COVID-19) below a risk threshold level, a processor may indicate that the employee may enter the workspace. For example, in embodiments where a processor determines, based on a user/employee's check-in questionnaire that the user/employee has an exposure risk level below the risk threshold level (e.g., is unlikely to have contracted COVID-19), the processor may indicate that they are allowed to enter the workspace by sending a notification (e.g., email or text message) to the user/employee, such as a green pass, indicating they may enter the workspace that day.

In some embodiments, where a processor may determine the employee does not have a low exposure risk level (e.g., has a high-risk level) the processor could recommend the employee work remotely or from home. For example, in embodiments where a processor determines a user/employee's exposure risk level exceeds a risk threshold level, the processor may send a notification, such as a red pass, indicating that they should not enter the workspace. In some embodiments, in order to reduce the number of people in the workspace, a processor may randomly select employees who will be able to work in the workplace and those who will be requested not enter the workspace. In embodiments where a processor has indicated the employee may enter the workspace, a processor may assign a workstation to the employee. In some embodiments, the check-in questionnaire may be received by an Artificial Intelligence (AI), such as Watson Works®. In embodiments, the AI may decide if the user/employee should be given a green pass or a red pass.

Reducing community spread of COVID-19 has had a variety of challenges. One significant challenge has been the spread of COVID-19 by asymptomatic carriers. Such carriers are often unaware that they have contracted the virus and continue participating in their daily routine without knowing they may be spreading the virus to those people they come into contact with. As a result, in some situations though the user/employee may be granted a green pass, some asymptomatic carriers may pose a risk to other users/employees in the workspace. As such, there is a need to reduce risk of spread in the workspace. As referenced herein, by assigning workstations to users/employees in a workspace based on risk may mitigate or reduce the spread of diseases, such as COVID-19, and may protect users/employees who are more susceptible.

In embodiments, a processor may generate a user profile for each of the one or more employees (e.g., users). Each of the respective user profiles may include user data associated with the respective user/employee. In embodiments, user data may be comprised of multiple data sources that are provided by the user/employee. These data sources may include, but are not limited to, user/employee provided health profile (e.g., lab data indicating the user/employee has tested negative for COVID-19) or information associated with the check-in questionnaire. In some embodiments, the user/employee may also provide the user/employee's age, their general health condition, preexisting conditions, and other health factors that could increase the user/employee's likelihood of negative side effects were they to contract the contagion. This user/employee provided information may be referred to as a susceptibility condition. In embodiments, a user profile may also indicate if the user/employee has received any relevant treatments (e.g., antibody treatment, vaccinations) associated with the disease (e.g., COVID-19). Each user profile may be configured within a database and may be made accessible to the processor. In embodiments, a processor may access the information in the user profiles and assign a respective risk level to each of the user profiles. In these embodiments, a processor may determine each user/employee's respective risk level by configuring how likely a user/employee is to come into contact with COVID-19 (e.g., is roommates with an essential worker) as well as how susceptible the user/employee might be to COVID-19. For example, those users/employees with one or more comorbidities (e.g., employees who are immunocompromised) may be more likely to suffer serious disease symptoms than those users/employees who do not have comorbidities.

In embodiments, a processor may generate and apply a user characteristic model. In these embodiments, the user characteristic model may be based, at least in part on the user profiles of each user/employee and the respective risk levels associated with the user profiles of each user/employees. In such embodiments, a user characteristic model may catalog the users/employees in a workspace (e.g., those given a green pass) based on their respective risk levels. In one example embodiment, a user characteristic model may catalog employee A, employee B, and employee C in a workspace. In this example embodiment, based on the relative risk level, a user characteristic model could indicate that employee C has a higher susceptibility than employees A and B, and that employee B has a higher susceptibility than employee A. Continuing this example embodiments, a user characteristic model could also indicate that employee A has a higher likelihood of contracting COVID-19 than employees B and C, and employee B has a higher likelihood of contracting COVID than employee C.

In embodiments, a processor may generate a workstation characteristics model of a workspace. A workstation characteristics model may include a layout of the different workstations in the workspace and determine a workstation risk level for each of the workstations in the workplace that are intended to be utilized by users/employees. A workstation may include, but is not limited to, desk, office, seat, cubicle, or area a user/employee may utilize in the workspace. In embodiments, a processor may generate a workstation characteristic model using various data sources. These data sources may include, but are not limited to, workstation coordinates in the workspace, workstation cleaning schedule (e.g., sterilizing the workstation), building maintenance (e.g., garbage removal or changing of a HVAC filter), direction of airflow over each workstation, intensity of airflow over each workstation in the workspace, and the positioning of the workstation with respect to the airflow.

In some embodiments, a processor may generate a workstation characteristic model using data collection devices (e.g., Internet of Things (IoT) sensor devices) and/or other devices utilized in smart buildings. In these embodiments, a processor may use the data collected from the data collection devices to render an airflow direction plan. An airflow direction plan may specify the flow of air throughout the workspace. Often, depending on the configuration of the workspace the airflow or direction of airflow may be different in one workstation when compared to another workstation in the same workspace. For example, the location of the workstation with respect to workspace components such as, walls or vents associated with a HVAC system, could result in one workstation having a different airflow pattern compared to the airflow patter in an adjacent workstation.

In embodiments, a processor may assign each of the one or more users to respective workstations. In some embodiments, a processor may base workstation assignment, at least in part, on the user characteristic model and the workstation characteristic model. In these embodiments, a processor may perform one or more statistical analysis and/or probability analyses, using the user characteristic model and the workstation characteristic model. By using one or more statistical and/or probability analysis the process may consider both a user/employee's likelihood of contracting the virus and their possible comorbidity, as well as how a user/employee's workstation assignment may increase or decrease COVID-19 transmission in the workplace. In some embodiments, a processor may send one or more notifications to users/employees to notify them of their assigned workstation assignment prior to their arrival to the workspace.

In one example embodiment, a processor may analyze the workstation characteristic model having three workstations (workstation 1, workstation 2, workstation 3) positioned next to each other in a workspace. The workstation characteristic model may include an airflow direction plan that indicates that air in the workspace is circulated from a vent positioned near workstation 1. In this example, the vent may force air to flow from workstation 1 to workstation 2, then to workstation 3. As is commonly understood, particularly with airborne diseases such as COVID-19, contagious particulates may be carried in the air. In such situation wind or airflow can cause contagious particulates originating from one person, to interact with one or more persons downwind or downstream. The processor may then analyze the user characteristic model having three users/employees (employee A, employee B, employee C). The user characteristic model may include information from each user/employee's respective user profile. The user characteristic model may indicate that employee A has a higher probability of contracting the disease than employees B and C (e.g., employee A has a spouse who is a frontline COVID-19 healthcare worker), and employee B has a higher probability of contracting the disease than employee C (e.g., employee C lives alone). The user characteristic model may also indicate that, while employee C has a higher risk of being susceptible (e.g., employee C has a known comorbidity) than employees A and B, employees A and B have the same risk of susceptibility. In this example embodiment, a processor may consider the airflow plan from the workstation characteristic model and determine that because employee C has the highest risk of negative side effects were they to contract the disease and lowest likelihood of contracting the disease that employee C should be assigned to workstation 1. If employees A and B unknowingly contract the disease and enter the workspace prior to exhibiting symptoms, but are positioned downwind from employee C, employee C is less likely to contract the disease from employees A and B. If employee C were assigned to workstation 3, employee C would likely be exposed to contagious particulates of the disease carried through the air via the vent airflow from employees A and B (e.g., were employees A and B assigned to workstation 1 and workstation 2).

Continuing the above example, the processor could assign employee B to workstation 2 and employee A to workstation 3. In this example, despite employees A and B having the same susceptibility to the disease, because employee A has a spouse who is a frontline worker, who due to their position are more likely to contract the disease and transmit the disease to employee A. Because employee A is more likely to contract the disease than employee B, to mitigate this risk, the processor may assign employee B to workstation 2 adjacent to workstation 3 but located upstream to employee A. While the above example depicts how a processor might assign workstations in a simplistic workspace, embodiments contemplated herein may be applied to any workspace configuration. These workspace configurations may include a workspace having multiple rooms where each room may include one or more workstations, workspaces having one or more airflow plans (e.g., air flowing from multiple directions in a room with more than one workstation), workspaces having partially opened spaces (e.g., a room with a partial room divider), or any combination thereof.

In some embodiments, a processor may be configured to set an employee risk threshold. While in some embodiments, the employee risk threshold is determined by an employer or owner of a workspace, in other embodiments, the employee risk threshold may be independently configured by health and safety guidelines provided by medical professionals. In these embodiments, a processor may consider a user/employee's total risk level and compare it to the employee risk threshold. A processor may determine a user/employee's total risk level based on the user characteristic model and the workstation characteristic model. For example, if a user/employee is severely immunocompromised and due to the workspace configuration (e.g., open concept workspace) a processor may determine that the user/employee cannot safely occupy the workspace. In this example, the user/employee could be assigned a high total risk level. In such embodiments, if a user/employee's total risk level exceeds the employee risk threshold, the user/employee will not be assigned a workstation (e.g., the user/employee's green pass may be revoked). In an alternative example, if a user/employee attends a public concert without social distancing during a pandemic, a processor may determine that this user/employee's total risk level exceeds the employee risk threshold because they could pose a risk to the other users/employees that cannot be mitigated by workstation assignment (e.g., because of the workspace configuration).

Referring now to FIG. 1, a block diagram of a workstation assignment system 100, is depicted in accordance with embodiments of the present disclosure. FIG. 1 provides an illustration of only one implementation and does not imply any limitations with regard to the environments in which different embodiments may be implemented. Many modifications to the depicted environment may be made by those skilled in the art without departing from the scope of the invention as recited by the claims.

In embodiments, workstation assignment system 100 may be configured to include user profile database 102, workstation profile database 104, user characteristic model 106, workstation characteristic model 108, and workstation assignment module 110. In embodiments, user profile database 102 may be configured to house or store each user/employee's respective user profile. In embodiments, workstation assignment system 100 may be configured to utilize the information in the user profiles to generate user characteristic model 106. In embodiments, user characteristic model 106 may include consider one or more risk levels associated with each user/employee.

In embodiments, workstation profile database 104 may be configured to house data/information associated with how the workplace is configured. In some embodiments, this data/information may be collected from one or more data collection devices configured in the workspace. In embodiments, workstation assignment system 100 may configure workstation profile database 104 to generate workstation characteristic model 108. In embodiments, workstation characteristic model 108 may include one or more airflow directions or currents (e.g., airflow direction plan) that may be controlled by a HVAC system in the workspace, the maximum number of users/employees that are allowed to occupy the workspace, coordinates of each workstation, and if workstations are upstream or downstream with respect to a particular airflow.

In embodiments, workstation assignment system 100 may configure workstation assignment module 110 to receive user characteristic model 106 and workstation characteristic model 108. In these embodiments, workstation assignment module 110 may process the data/information associated with user characteristic model 106 and the workstation characteristic model 108 to assign workspaces that mitigate or reduce the spread of COVID-19 and other similar diseases in the workplace.

Figure 2:
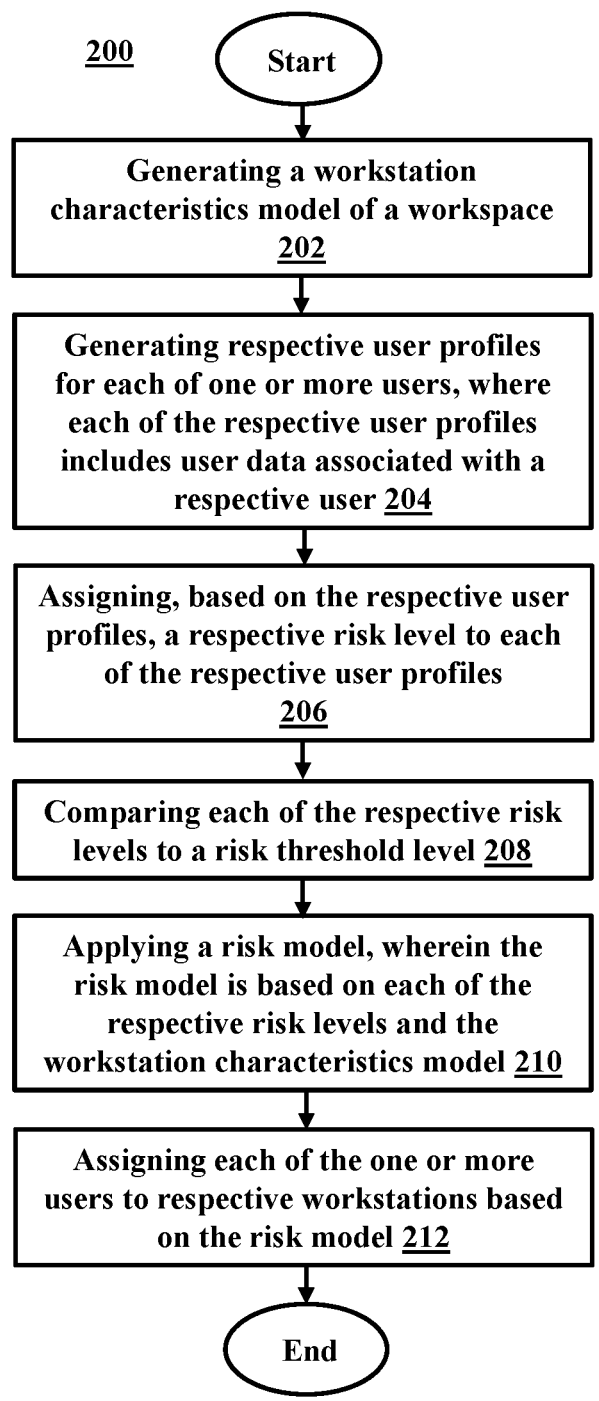
FIG. 2 illustrates a flowchart of a method for assigning workstations, in accordance with embodiments of the present disclosure.

Referring now to FIG. 2, a flowchart illustrating an example method 200 for assigning workstations, in accordance with embodiments of the present disclosure. In some embodiments, the method 200 begins at operation 202 where a processor generates a workstation characteristics model of a workspace.

In some embodiments, the method 200 proceeds to operation 204. At operation 204, a processor may generate respective user profiles for each of one or more users, each of the respective user profiles may include user data associated with a respective user.

In some embodiments, the method 200 proceeds to operation 206. At operation 206, the processor may assign, based on the respective user profiles, a respective risk level to each of the respective user profiles.

In some embodiments, the method 200 proceeds to operation 208. At operation 208, the processor may compare each of the respective risk levels to a risk threshold level. In some embodiments, the method 200 proceeds to operation 210. At operation 210, the processor may apply a user characteristic model. In embodiments, the user characteristic model may be based on each of the respective risk levels and the workstation characteristics model.

In some embodiments, the method 200 proceeds to operation 212. At operation 212, the processor may assign each of the one or more users to respective workstations based on the user characteristic model. In some embodiments, as depicted in FIG. 2, after operation 210, the method 200 may end.

As discussed in more detail herein, it is contemplated that some or all of the operations of the method 200 may be performed in alternative orders or may not be performed at all; furthermore, multiple operations may occur at the same time or as an internal part of a larger process.

It is to be understood that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of portion independence in that the consumer generally has no control or knowledge over the exact portion of the provided resources but may be able to specify portion at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 3A:
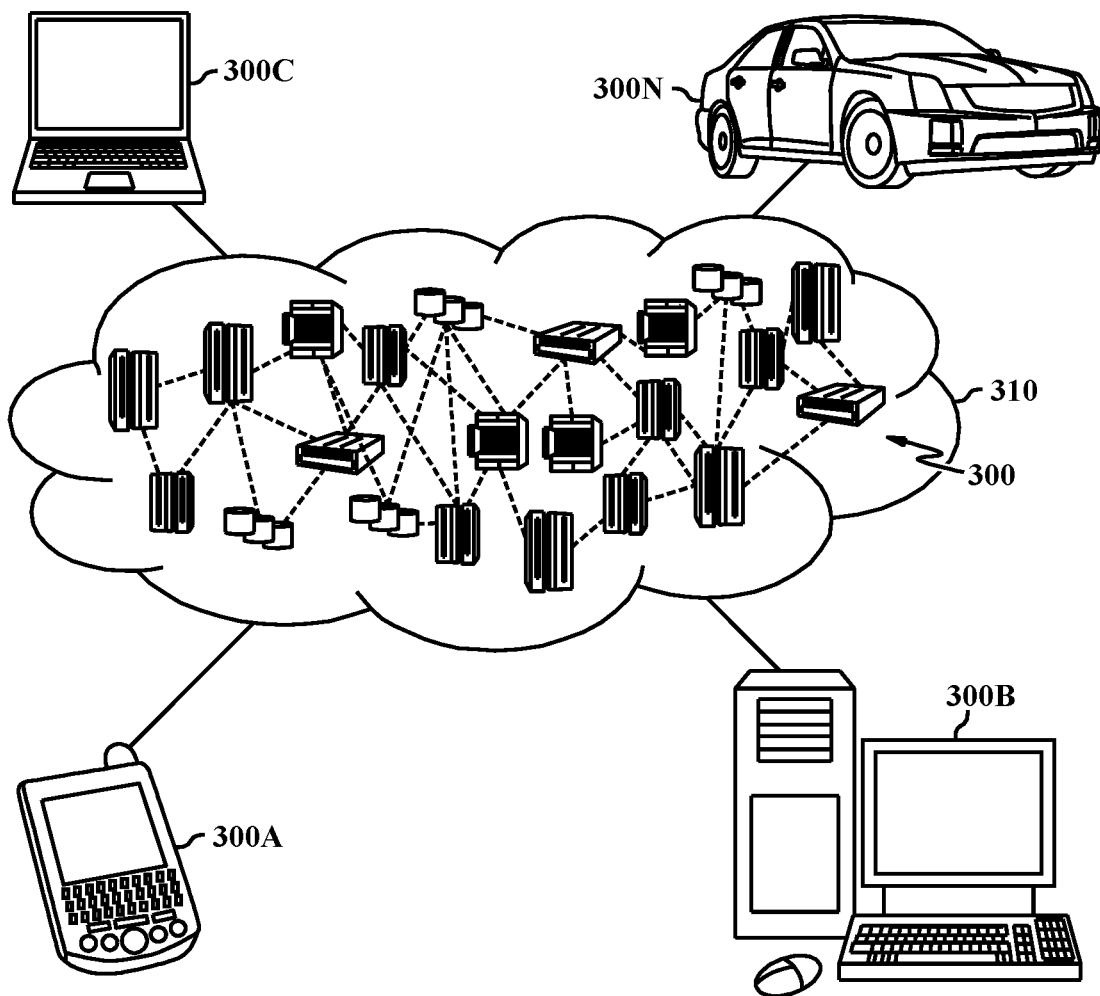
FIG. 3A illustrates a cloud computing environment, in accordance with embodiments of the present disclosure.

Referring now to FIG. 3A, illustrative cloud computing environment 310 is depicted. As shown, cloud computing environment 310 includes one or more cloud computing nodes 300 with which local computing devices used by cloud consumers, such as, for example, personal digital assistant (PDA) or cellular telephone 300A, desktop computer 300B, laptop computer 300C, and/or automobile computer system 300N may communicate. Nodes 300 may communicate with one another. They may be grouped (not shown) physically or virtually, in one or more networks, such as Private, Community, Public, or Hybrid clouds as described hereinabove, or a combination thereof. This allows cloud computing environment 310 to offer infrastructure, platforms and/or software as services for which a cloud consumer does not need to maintain resources on a local computing device. It is understood that the types of computing devices 300A-N shown in FIG. 3A are intended to be illustrative only and that computing nodes 300 and cloud computing 300 and cloud computing environment 310 can communicate with any type of computerized device over any type of network and/or network addressable connection (e.g., using a web browser).

Figure 3B:
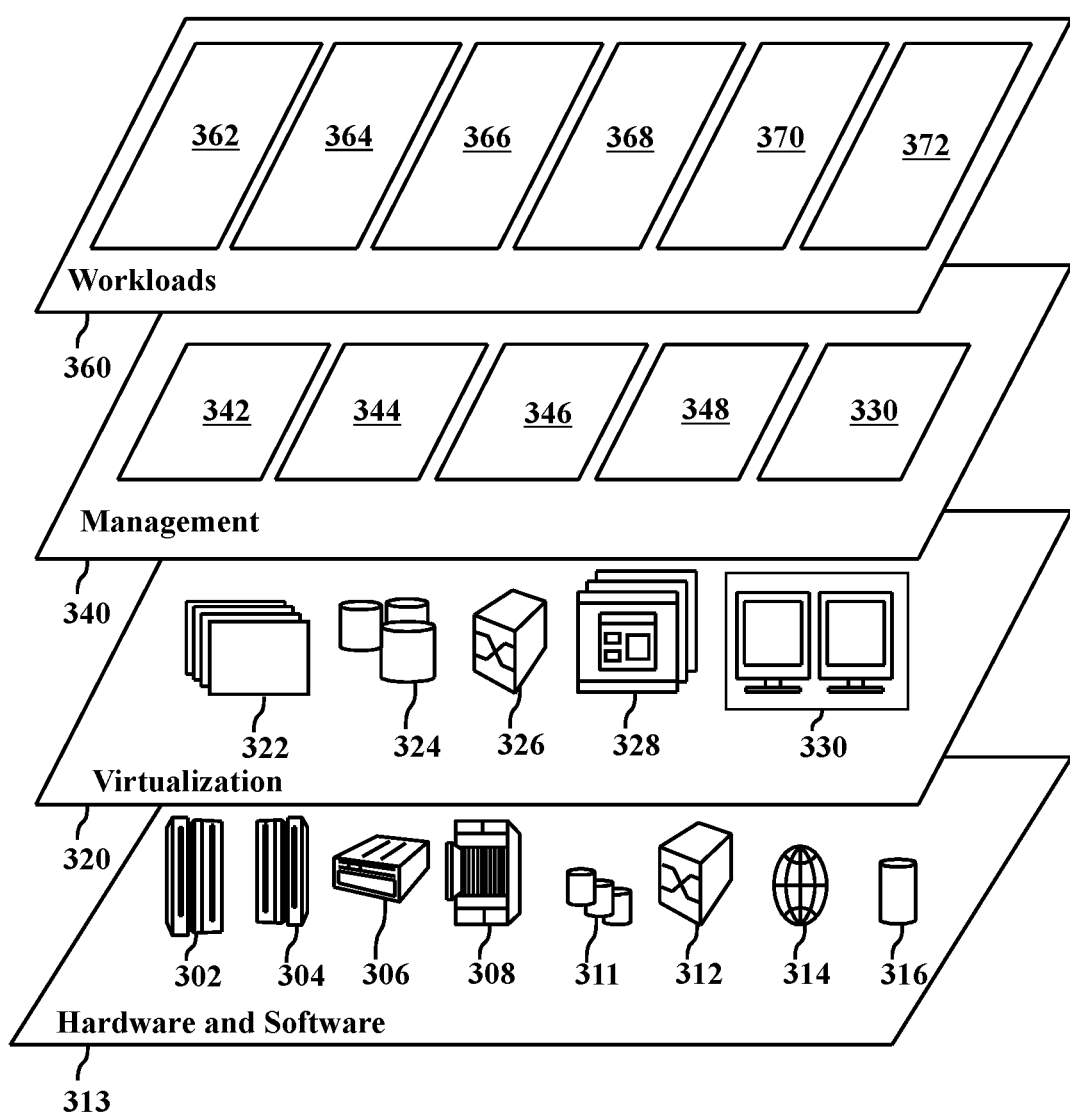
FIG. 3B illustrates abstraction model layers, in accordance with embodiments of the present disclosure.

Referring now to FIG. 3B, a set of functional abstraction layers provided by cloud computing environment 310 (FIG. 3A) is shown. It should be understood in advance that the components, layers, and functions shown in FIG. 3B are intended to be illustrative only and embodiments of the disclosure are not limited thereto. As depicted below, the following layers and corresponding functions are provided.

Hardware and software layer 315 includes hardware and software components. Examples of hardware components include: mainframes 302; RISC (Reduced Instruction Set Computer) architecture based servers 304; servers 306; blade servers 308; storage devices 311; and networks and networking components 312. In some embodiments, software components include network application server software 314 and database software 316.

Virtualization layer 320 provides an abstraction layer from which the following examples of virtual entities may be provided: virtual servers 322; virtual storage 324; virtual networks 326, including virtual private networks; virtual applications and operating systems 328; and virtual clients 330.

In one example, management layer 340 may provide the functions described below. Resource provisioning 342 provides dynamic procurement of computing resources and other resources that are utilized to perform tasks within the cloud computing environment. Metering and Pricing 344 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 346 provides access to the cloud computing environment for consumers and system administrators. Service level management 348 provides cloud computing resource allocation and management such that required service levels are met. Service Level Agreement (SLA) planning and fulfillment 350 provide pre-arrangement for, and procurement of, cloud computing resources for which a future requirement is anticipated in accordance with an SLA.

Workloads layer 360 provides examples of functionality for which the cloud computing environment may be utilized. Examples of workloads and functions which may be provided from this layer include: mapping and navigation 362; software development and lifecycle management 364; virtual classroom education delivery 366; data analytics processing 368; transaction processing 370; and controlling air quality in enclosed places 372.

Figure 4:
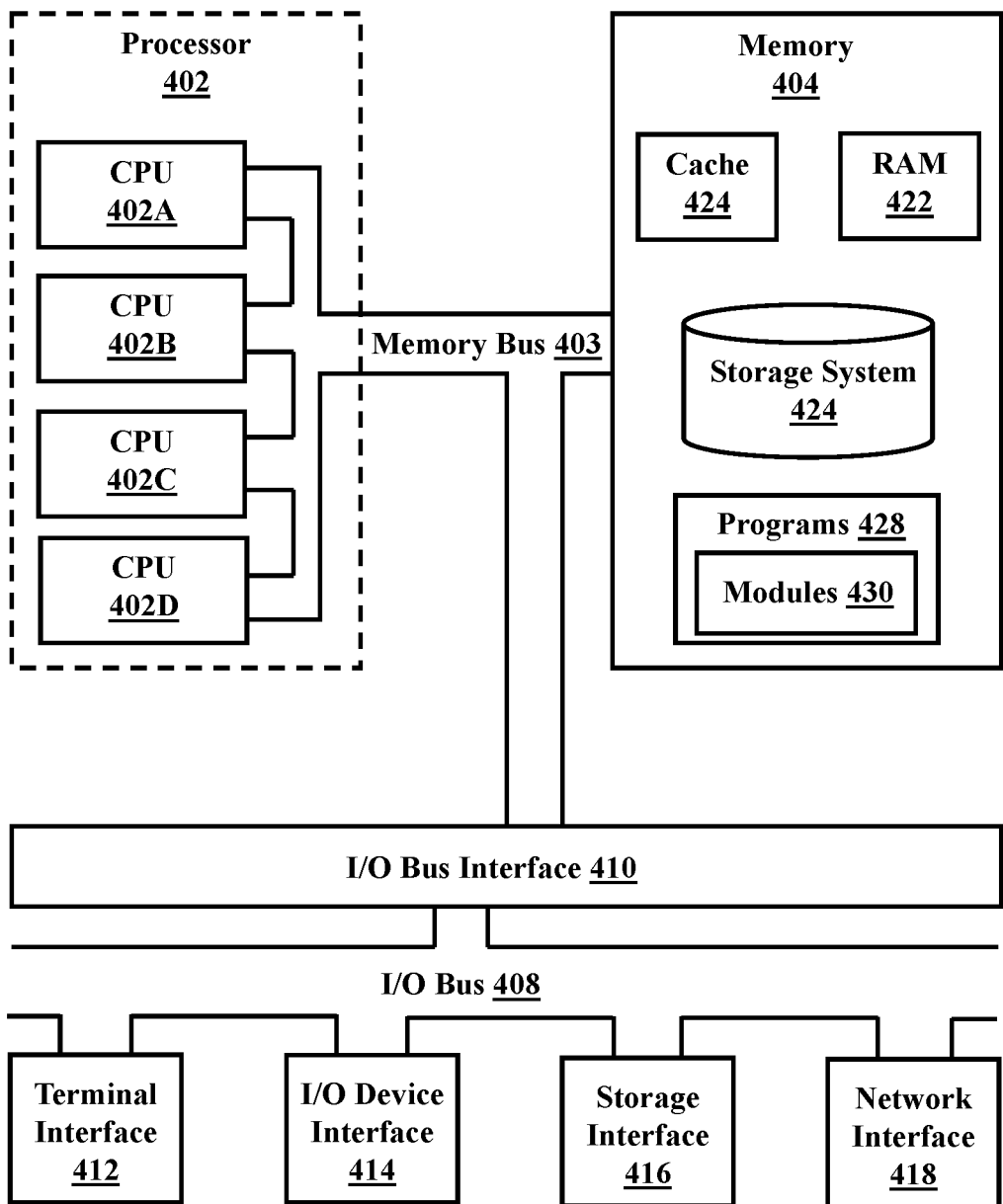
FIG. 4 illustrates a high-level block diagram of an example computer system that may be used in implementing one or more of the methods, tools, and modules, and any related functions, described herein, in accordance with embodiments of the present disclosure.

FIG. 4, illustrated is a high-level block diagram of an example computer system 401 that may be used in implementing one or more of the methods, tools, and modules, and any related functions, described herein (e.g., using one or more processor circuits or computer processors of the computer), in accordance with embodiments of the present invention. In some embodiments, the major components of the computer system 401 may comprise one or more Processor 402, a memory subsystem 404, a terminal interface 412, a storage interface 416, an I/O (Input/Output) device interface 414, and a network interface 418, all of which may be communicatively coupled, directly or indirectly, for inter-component communication via a memory bus 403, an I/O bus 408, and an I/O bus interface unit 410.

The computer system 401 may contain one or more general-purpose programmable central processing units (CPUs) 402A, 402B, 402C, and 402D, herein generically referred to as the CPU 402. In some embodiments, the computer system 401 may contain multiple processors typical of a relatively large system; however, in other embodiments the computer system 401 may alternatively be a single CPU system. Each CPU 402 may execute instructions stored in the memory subsystem 404 and may include one or more levels of on-board cache.

System memory 404 may include computer system readable media in the form of volatile memory, such as random access memory (RAM) 422 or cache memory 424. Computer system 401 may further include other removable/non-removable, volatile/non-volatile computer system storage media. By way of example only, storage system 426 can be provided for reading from and writing to a non-removable, non-volatile magnetic media, such as a "hard drive." Although not shown, a magnetic disk drive for reading from and writing to a removable, non-volatile magnetic disk (e.g., a "floppy disk"), or an optical disk drive for reading from or writing to a removable, non-volatile optical disc such as a CD-ROM, DVD-ROM or other optical media can be provided. In addition, memory 404 can include flash memory, e.g., a flash memory stick drive or a flash drive. Memory devices can be connected to memory bus 403 by one or more data media interfaces. The memory 404 may include at least one program product having a set (e.g., at least one) of program modules that are configured to carry out the functions of various embodiments.

One or more programs/utilities 428, each having at least one set of program modules 430 may be stored in memory 404. The programs/utilities 428 may include a hypervisor (also referred to as a virtual machine monitor), one or more operating systems, one or more application programs, other program modules, and program data. Each of the operating systems, one or more application programs, other program modules, and program data or some combination thereof, may include an implementation of a networking environment. Programs 428 and/or program modules 430 generally perform the functions or methodologies of various embodiments.

Although the memory bus 403 is shown in FIG. 4 as a single bus structure providing a direct communication path among the CPUs 402, the memory subsystem 404, and the I/O bus interface 410, the memory bus 403 may, in some embodiments, include multiple different buses or communication paths, which may be arranged in any of various forms, such as point-to-point links in hierarchical, star or web configurations, multiple hierarchical buses, parallel and redundant paths, or any other appropriate type of configuration. Furthermore, while the I/O bus interface 410 and the I/O bus 408 are shown as single respective units, the computer system 401 may, in some embodiments, contain multiple I/O bus interface units 410, multiple I/O buses 408, or both. Further, while multiple I/O interface units are shown, which separate the I/O bus 408 from various communications paths running to the various I/O devices, in other embodiments some or all of the I/O devices may be connected directly to one or more system I/O buses.

In some embodiments, the computer system 401 may be a multi-user mainframe computer system, a single-user system, or a server computer or similar device that has little or no direct user interface, but receives requests from other computer systems (clients). Further, in some embodiments, the computer system 401 may be implemented as a desktop computer, portable computer, laptop or notebook computer, tablet computer, pocket computer, telephone, smartphone, network switches or routers, or any other appropriate type of electronic device.

It is noted that FIG. 4 is intended to depict the representative major components of an exemplary computer system 401. In some embodiments, however, individual components may have greater or lesser complexity than as represented in FIG. 4, components other than or in addition to those shown in FIG. 4 may be present, and the number, type, and configuration of such components may vary.

As discussed in more detail herein, it is contemplated that some or all of the operations of some of the embodiments of methods described herein may be performed in alternative orders or may not be performed at all; furthermore, multiple operations may occur at the same time or as an internal part of a larger process.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Although the present invention has been described in terms of specific embodiments, it is anticipated that alterations and modification thereof will become apparent to the skilled in the art. Therefore, it is intended that the following claims be interpreted as covering all such alterations and modifications as fall within the true spirit and scope of the disclosure.

What is claimed is:

1. A computer-implemented method comprising:
   collecting, via sensors of a workspace having one or more workstations, data about the workspace, the data including at least one member selected from a group consisting of airflow over each workstation, intensity of airflow over each workstation, and positioning of the workstation with respect to the airflow;
   generating, by a processor and based on the collected data, a workstation characteristics model for the workspace, the workstation characteristics model comprising an airflow direction plan for the workspace;
   receiving user data associated with users, wherein the user data is received by way of a questionnaire administered by an artificial intelligence agent;
   analyzing, by the processor, the user data associated with the users to identify a respective risk level for the users;
   generating a user characteristic model based on the risk levels of the users, the user characteristic model producing a ranking of respective risk levels for the users, a first user having a highest risk level of the users;
   storing the collected data, the workstation characteristics model, and the user characteristic model in a network-connected storage device;
   analyzing the user characteristic model and the workstation characteristic model to identify a likelihood of transmission, the analyzing including statistical and probability analysis;
   assigning some of the users to a particular workstation from the one or more workstations, wherein the assigning reduces the likelihood of transmission and is based on placing a first user in a workstation in a most upstream position of the airflow direction plan in the workspace;
   assigning via the user characteristic model and the workstation characteristic model a respective user pass for allowing or denying permission to all of the users to visit the workspace for a respective time period, wherein a first user pass for the first user grants permission to enter the workspace and includes the workstation assignment for the most upstream position of the airflow direction plan in the workspace, a second user pass for a second user denies permission to enter and instructs the second user to work remotely, and a third user pass for a third user is randomly selected and denies permission to enter and instructs the third user to work remotely; and
   transmitting, over a computer network and in real time and as part of notifications, the user passes including the first, second, and third user passes to computers respectively associated with the users so that all of the users have immediate access to up-to-date user pass information about visiting the workspace for the time period.

2. The method of claim 1, wherein the workstation characteristics model of the workspace includes seat coordinates and a desk cleaning schedule.

3. The method of claim 1, wherein the user characteristic model is based, at least in part, on susceptibility conditions of the users.

4. The method of claim 1, wherein the user characteristic model is based, at least in part, on building maintenance.

5. The method of claim 1, wherein, for all those notifications going to those of the users whose respective user pass allows permission to visit the workspace for the respective time period, the respective notifications include a respective workstation assignment.

6. The method of claim 1, wherein a flow of air in the airflow plan at a first workstation is different from a flow of air in a second workstation of the one or more workstations.

7. The method of claim 1, wherein the sensors comprise Internet of Things sensors.

8. A system comprising:
   a memory;
   sensors; and
   a processor in communication with the memory and the sensors, the processor being configured to perform operations comprising:
      collecting, via the sensors distributed in a workspace having one or more workstations, data about the workspace, the data including at least one member selected from a group consisting of airflow over each workstation, intensity of airflow over each workstation, and positioning of the workstation with respect to the airflow;
      generating, based on the collected data, a workstation characteristics model for the workspace, the workstation characteristics model comprising an airflow direction plan for the workspace;

receiving user data associated with users;

analyzing the user data associated with the users to identify a respective risk level for the users;

generating a user characteristic model based on the risk levels of the users, the user characteristic model producing a ranking of respective risk levels for the users, a first user having a highest risk level of the users;

storing the collected data, the workstation characteristics model, and the user characteristic model in a network-connected storage device;

analyzing the user characteristic model and the workstation characteristic model to identify a likelihood of transmission, the analyzing including statistical and probability analysis;

assigning some of the users to a particular workstation from the one or more workstations, wherein the assigning reduces the likelihood of transmission and is based on placing the first user in a workstation in a most upstream position of the airflow direction plan in the workspace;

assigning via the user characteristic model and the workstation characteristic model a respective user pass for allowing or denying permission to all of the users to visit the workspace for a respective time period, wherein a first user pass for the first user grants permission to enter the workspace and includes the workstation assignment for the most upstream position of the airflow direction plan in the workspace, a second user pass for a second user denies permission to enter and instructs the second user to work remotely, and a third user pass for a third user is randomly selected and denies permission to enter and instructs the third user to work remotely; and transmitting, over a computer network and in real time and as part of a notifications, the user passes including the first, second, and third user passes to computers respectively associated with the users so that all of the users have immediate access to up-to-date user pass information about visiting the workspace for the time period.

9. The system of claim 8, wherein the workstation characteristics model of the workspace includes seat coordinates and a desk cleaning schedule.

10. The system of claim 8, wherein the user characteristic model is based, at least in part, on susceptibility conditions of the users.

11. The system of claim 8, wherein the user characteristic model is based, at least in part, on building maintenance.

12. The system of claim 8, wherein, for all those notifications going to those of the users whose respective user pass allows permission to visit the workspace for the respective time period, the respective notifications include a respective workstation assignment.

13. The system of claim 8, wherein a flow of air in the airflow plan at a first workstation is different from a flow of air in a second workstation of the one or more workstations.

14. The computer system of claim 8, wherein the sensors comprise Internet of Things sensors.

15. A computer program product comprising a computer readable storage medium having program instructions embodied therewith, the program instructions executable by a processor to cause the processor to perform a method comprising:

collecting, via sensors of a workspace having one or more workstations, data about the workspace, the data including at least one member selected from a group consisting of airflow over each workstation, intensity of airflow over each workstation, and positioning of the workstation with respect to the airflow;

generating, based on the collected data, a workstation characteristics model for the workspace, the workstation characteristics model comprising an airflow direction plan for the workspace;

receiving user data associated with users, wherein the user data is received by way of a questionnaire administered by an artificial intelligence agent;

analyzing the user data associated with the users to identify a respective risk level for the users;

generating a user characteristic model based on the risk levels of the users, the user characteristic model producing a ranking of respective risk levels for the users, a first user having a highest risk level of the users;

storing the collected data, the workstation characteristics model, and the user characteristic model in a network-connected storage device;

analyzing the user characteristic model and the workstation characteristic model to identify a likelihood of transmission, the analyzing including statistical and probability analysis;

assigning some of the users to a particular workstation from the one or more workstations, wherein the assigning reduces the likelihood of transmission and is based on placing the first user in a workstation in a most upstream position of the airflow direction plan in the workspace;

assigning via the user characteristic model and the workstation characteristic model a respective user pass for allowing or denying permission to all of the users to visit the workspace for a respective time period, wherein a first user pass for the first user grants permission to enter the workspace and includes the workstation assignment for the most upstream position of the airflow direction plan in the workspace, a second user pass for a second user denies permission to enter and instructs the second user to work remotely, and a third user pass for a third user is randomly selected and denies permission to enter and instructs the third user to work remotely; and transmitting, over a computer network and in real time and as part of notifications, the user passes including the first, second, and third user passes to computers respectively associated with the users so that all of the users have immediate access to up-to-date user pass information about visiting the workspace for the time period.

16. The computer program product of claim 15, wherein the workstation characteristics model of the workspace includes seat coordinates and a desk cleaning schedule.

17. The computer program product of claim 15, wherein the user characteristic model is based, at least in part, on susceptibility conditions of the users.

18. The computer program product of claim 15, wherein the user characteristic model is based, at least in part, on building maintenance.

19. The computer program product of claim 15, wherein, for all those notifications going to those of the users whose respective user pass allows permission to visit the workspace for the respective time period, the respective notifications include a respective workstation assignment.

20. The computer program product of claim 15, wherein a flow of air in the airflow plan at a first workstation is different from a flow of air in a second workstation of the one or more workstations.

* * * * *